(12) United States Patent
Koenig et al.

(10) Patent No.: US 6,645,161 B2
(45) Date of Patent: Nov. 11, 2003

(54) METHOD, APPARATUS AND SIMULATED HUMAN TISSUE FOR EVALUATING COEFFICIENTS OF FRICTION OF MATERIALS ON HUMAN SKIN

(75) Inventors: David W. Koenig, Menasha, WI (US); Betsy L. Sadenwasser, Appleton, WI (US); Paul J. Koehler, Green Bay, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 43 days.

(21) Appl. No.: 10/021,286

(22) Filed: Dec. 12, 2001

(65) Prior Publication Data

US 2003/0109811 A1 Jun. 12, 2003

(51) Int. Cl.[7] .......................... A61B 5/103; A61B 5/117
(52) U.S. Cl. ....................................... 600/587
(58) Field of Search ................. 600/587, 350; 424/59, 60, DIG. 25, 423, 424, 484; 514/458, 474, 588, 725; 623/15.12, 901; 128/DIG. 8

(56) References Cited

U.S. PATENT DOCUMENTS

| 4,695,452 A | * | 9/1987 | Gannis et al. ................. 424/59 |
| 5,005,567 A | | 4/1991 | Gilman et al. |
| 5,350,583 A | * | 9/1994 | Yoshizato et al. ........ 623/15.12 |
| 5,601,530 A | | 2/1997 | Nielsen et al. |
| 5,611,859 A | | 3/1997 | Nielsen et al. |
| 5,782,819 A | | 7/1998 | Tanzer et al. |
| 5,795,320 A | | 8/1998 | Nielsen et al. |
| 5,948,707 A | | 9/1999 | Crawley et al. |
| 5,984,888 A | | 11/1999 | Nielsen et al. |
| 6,016,570 A | | 1/2000 | Vande Pol et al. |
| 6,139,848 A | | 10/2000 | Ahmad et al. |

FOREIGN PATENT DOCUMENTS

| EP | 0 965 834 A1 | 12/1999 |
| FR | 2 790 656 A1 | 3/1999 |
| WO | WO 00/51662 A1 | 9/2000 |

* cited by examiner

*Primary Examiner*—Max F. Hindenburg
*Assistant Examiner*—Brian Scott Szmal
(74) *Attorney, Agent, or Firm*—Senniger, Powers, Leavitt & Roedel (57) ABSTRACT

An in vitro testing method for predicting a coefficient of friction exhibited by a material passed over human skin, in vivo. A material operatively connects between a scaffold and a load cell and a synthetic sheet mounts on the scaffold. A porous layer is applied to an exposed surface of the synthetic sheet, forming a simulated human tissue. The material engages the simulated human tissue and moves relative to the scaffold to measure the coefficient of friction between the material and the simulated human tissue with the load cell.

15 Claims, 5 Drawing Sheets

METHOD, APPARATUS AND SIMULATED HUMAN TISSUE FOR EVALUATING COEFFICIENTS OF FRICTION OF MATERIALS ON HUMAN SKIN

BACKGROUND OF THE INVENTION

The present invention relates to an apparatus for simulating the friction of a material passing over human skin by performing an in vitro test without human skin. More specifically, this invention relates to an apparatus incorporating a simulated human tissue having a synthetic sheet and a porous layer which simulate the properties of human skin, including frictional resistance.

Friction is an important measure in the field of personal care products, such as facial tissue, bath tissue and baby wipes and for any product that contacts human skin during use. As friction between human skin and a product increases, the likelihood of causing damage to the skin increases. Further, determining the frictional properties of a particular product yields information about the way the product will feel on skin during use.

In the past, determining the coefficient of friction of a particular product on human skin required a friction test on a human subject. Experimentation on human subjects limits the potential number and variety of tests which may be administered. Moreover, tests requiring the use of unpleasant soiling agents or potentially uncomfortable products are difficult, if not impossible, to administer. Previous attempts to correlate in vitro testing to in vivo testing using a synthetic sheet or an organic skin have been generally unsuccessful. For example, silicone sheet as a substitute for human skin does not provide a proper correlation. Organic skins, such as porcine skin and snake skin, have also been tested as substitutes for human skin, without success. As such, there is a need for a test which will yield accurate friction measurements, without the need for an abundant supply of human subjects for testing. Because of the limitations of testing on human subjects, a substitute for human skin, which performs like human skin in friction coefficient testing, is needed.

SUMMARY OF THE INVENTION

Briefly, the present invention includes an in vitro testing method for predicting a coefficient of friction exhibited by a material passed over human skin, in vivo. A material is operatively connected between a scaffold and a load cell and a synthetic sheet is mounted on the scaffold. A porous layer is applied to an exposed surface of the synthetic sheet to form a simulated human tissue. The material engages the simulated human tissue. The method further comprises moving the material relative to the scaffold thereby to measure the coefficient of friction between the material and the simulated human tissue with the load cell.

In another aspect, the invention includes a simulated human tissue for evaluating the coefficient of friction between a material and the simulated human tissue to approximate the coefficient of friction that would be developed between the material and natural human skin.

In yet another aspect, the present invention includes a testing apparatus for evaluating a coefficient of friction. The testing apparatus comprises a scaffold sized and shaped to simulate a portion of human anatomy, a synthetic sheet and a load cell.

Other features of the present invention will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION OF THE PREFERRED EMBODIMENTS

Generally speaking, frictional forces occur between any two contacting bodies where there are forces tending to slide one of the bodies relative to the other. The frictional forces act parallel to the contacting surfaces and opposite the forces tending to cause sliding between the bodies. Further, the frictional forces are proportional to normal forces on the bodies, causing them to remain in contact. Coefficient of friction is defined as the ratio of the frictional force between the bodies to the normal force between the bodies. The coefficient of friction is different between bodies at rest and bodies moving relative to each other. In general, two bodies contacting one another, but not moving relative to one another, will exhibit greater frictional resistance to motion than bodies which are moving relative to one another. Hence, a coefficient of static friction (i.e., coefficient of friction between bodies which are not moving relative to each other) is generally greater than a coefficient of kinetic friction (i.e., coefficient of friction between bodies which are moving relative to each other). By experimentally determining these coefficients, the interaction of two bodies with respect to one another may be better defined.

Coefficient of friction is a commonly used measure of frictional forces between two bodies. Larger frictional coefficients correspond to larger amounts of friction between bodies, while smaller frictional coefficients correspond to smaller amounts of friction. In the case of products touching human skin, higher coefficients of friction cause higher shear forces at the skin surface, which can damage the skin and/or cause discomfort. Shear forces commonly occur during the cleaning of soil from human skin by wipes, towels and tissues. Further, as moisture on the skin increases, friction and shear forces increase.

Figure 1:
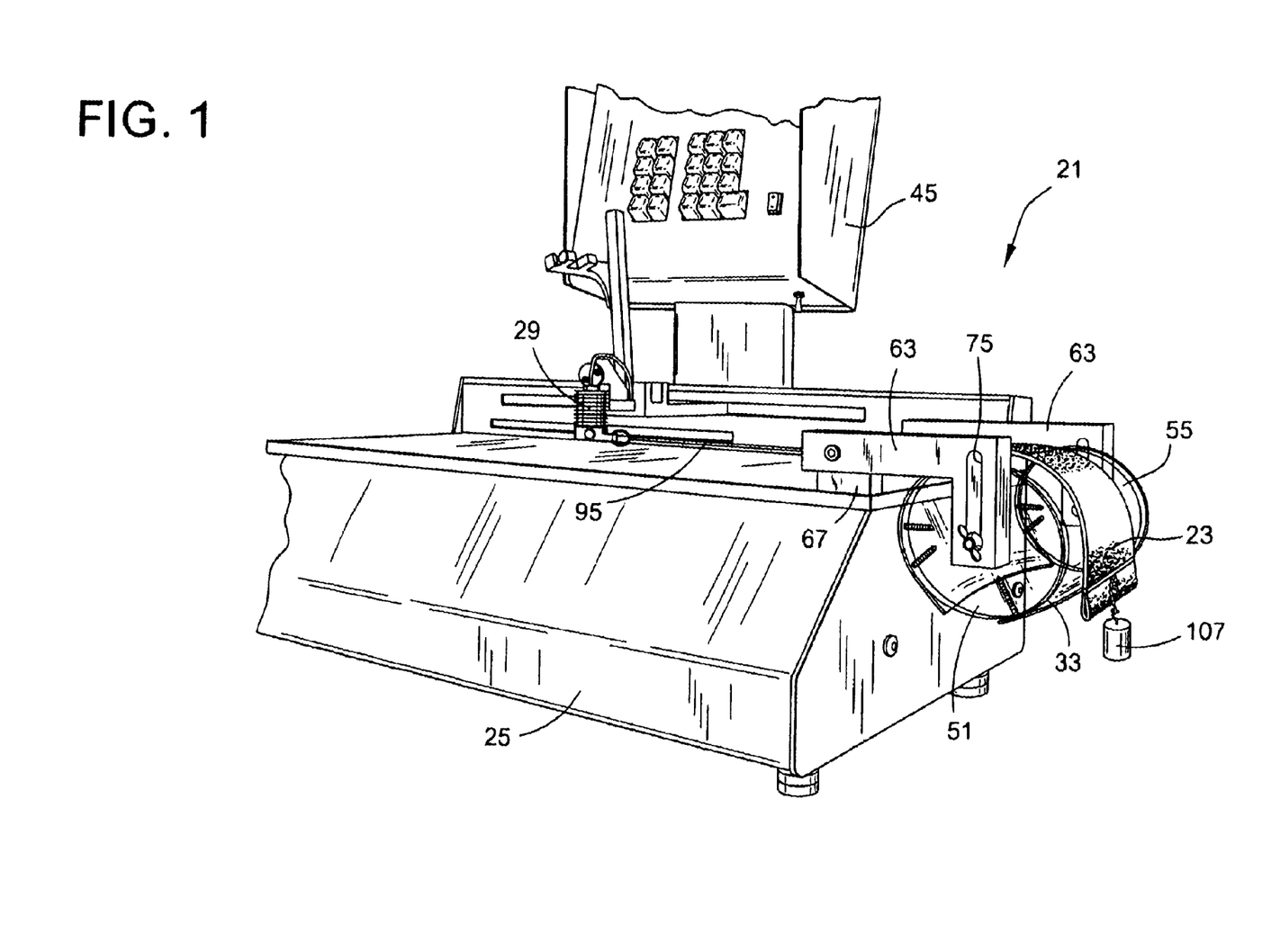
FIG. 1 is a perspective of an in vitro testing apparatus of the present invention.
Figure 2:
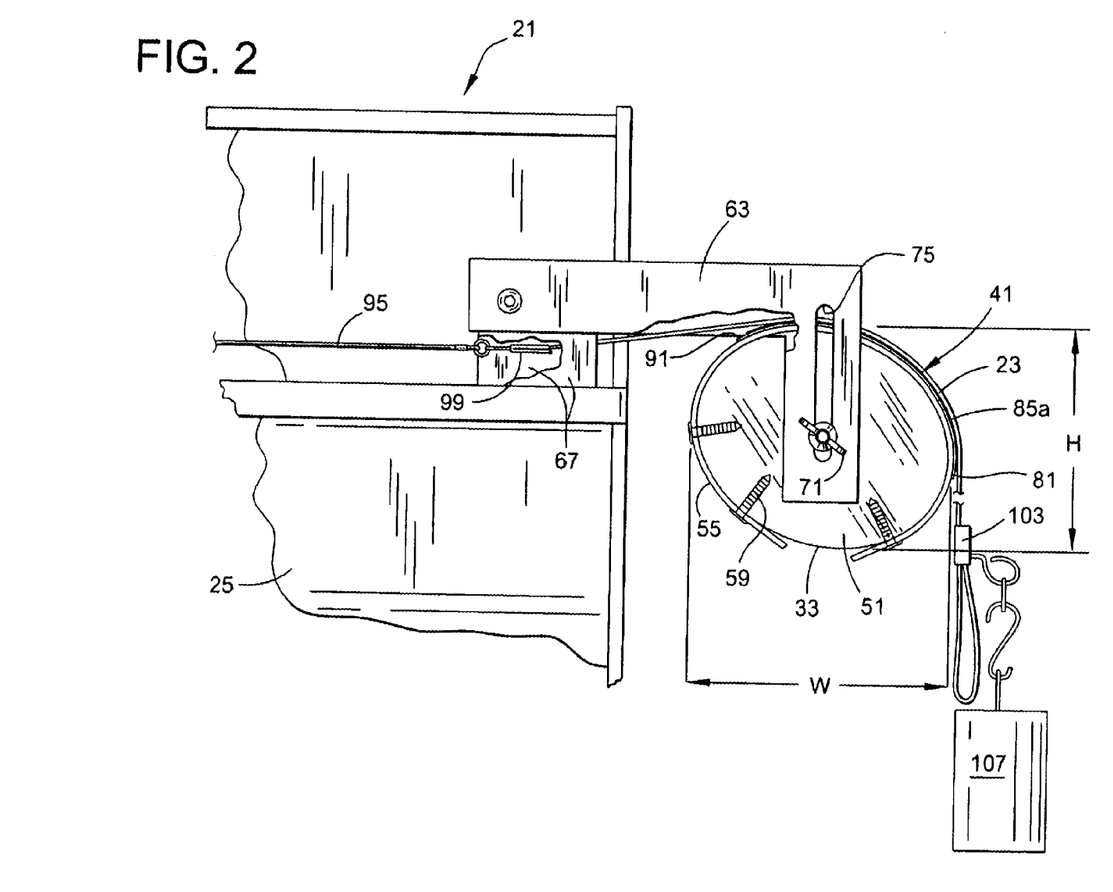
FIG. 2 is a partial front elevation of the apparatus of FIG. 1 with a sheet-like substance applied to an exposed surface of a synthetic sheet.
Figure 3:
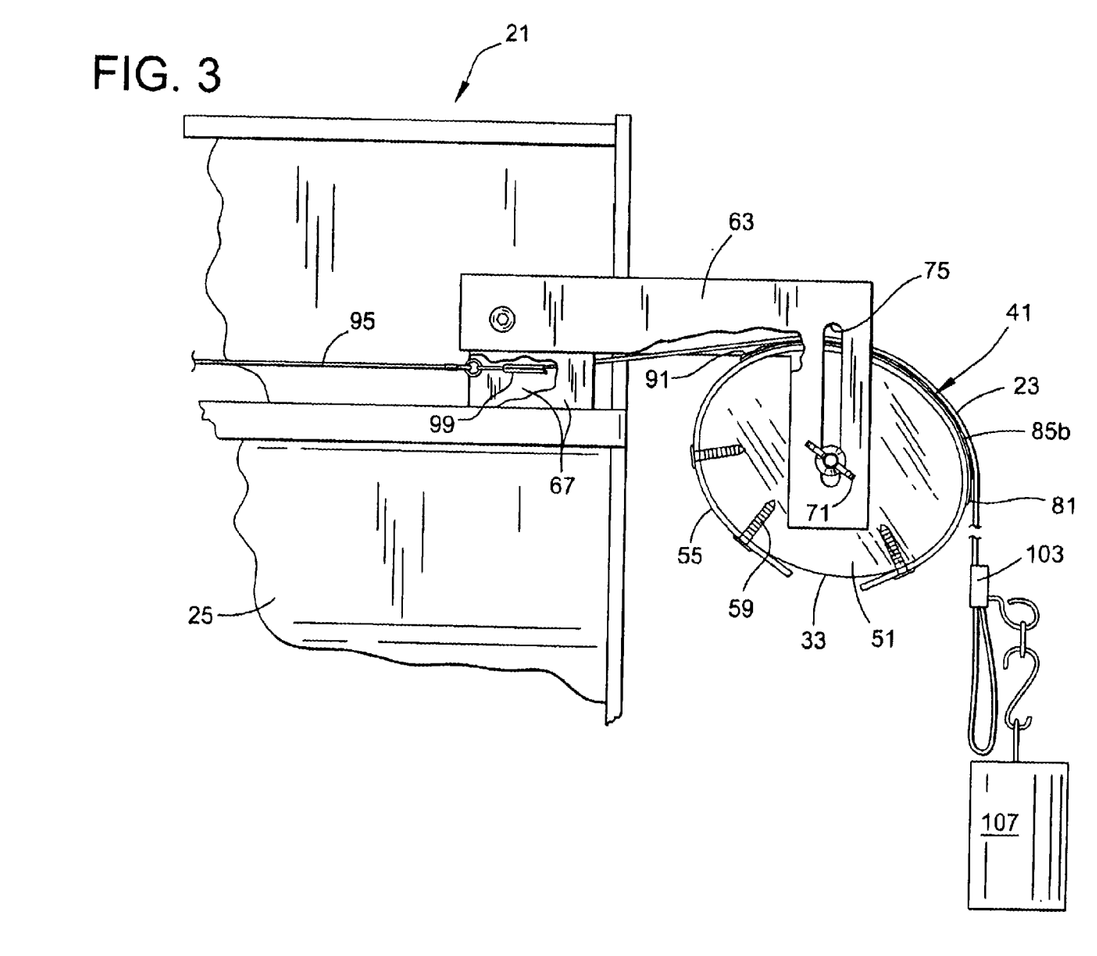
FIG. 3 is a partial front elevation of the apparatus of FIG. 1 with a barrier cream applied to an exposed surface of a synthetic sheet.

Referring now to the drawings and more particularly to FIGS. 1–3, an apparatus, designated in its entirety by the reference number 21, for predicting a coefficient of friction exhibited by a material 23 passed over human skin is shown.

In general, the testing apparatus 21 includes a base 25, a load cell 29 attached to the base for measuring force, a scaffold 33 attached to the base for supporting a simulated human tissue, generally indicated 41, and a control unit 45 for controlling the parameters of the testing apparatus and obtaining load measurements. The base 25, load cell 29 and control unit 45 are conventional and are readily understood by those skilled in the art. For example, the base 25, load cell 29 and control unit 45 employed in the examples discussed below are a Monitor/Slip and Friction™, Catalog Number 32-06, available from Testing Machines Inc. of Amityville, N.Y., U.S.A.

The scaffold 33 is sized and shaped to simulate a portion of human anatomy to improve the correlation between the simulated human tissue 41 and human skin. It is contemplated that the scaffold 33 may resemble any variety of human anatomy shapes without departing from the scope of the present invention. For example, in one embodiment, the scaffold 33 is sized and shaped to simulate a human arm, specifically a human forearm. Such a scaffold 33 is generally cylindrical in shape, having a generally horizontal axis. The scaffold 33 includes two end caps 51 defining the ends of the scaffold and a testing surface 55 extending between the end caps, thereby defining the cylindrical wall of the scaffold. The testing surface 55 may be formed from a thin, flat material wrapped around the end caps 51 and secured to the end caps with fasteners, such as screws 59. The scaffold 33 may be of unitary construction or formed from multiple additional portions without departing from the scope of the present invention. Brackets 63 extend from the base 25 to mount the scaffold 33 on the apparatus 21. The brackets 63 mount on the base 25 via flanges 67 extending from the base. The end caps 51 preferably mount on the brackets 63 with fasteners 71, such as wing nuts or wing screws (not shown). The brackets 63 may include slots 75 for receiving the fasteners 71, so that the scaffold 33 position may be adjusted relative to the base 25 along the slots.

To more closely simulate human arm anatomy, the scaffold 33 desirably has an oval cross-section. In one embodiment, the scaffold 33 has a height H of about 7.6 centimeters and a width W of about 10 centimeters (FIG. 2). Furthermore, the scaffold 33 has a length of about 22.2 centimeters. The scaffold 33 may be formed from any substance capable of holding its shape during testing. Suitable scaffold 33 substances include, but are not limited to, plastic, metal and stiff cardboard. One suitable scaffold 33 comprises a clear, plastic tube formed from Lexan® plastic, available from General Electric Company, Schenectady, N.Y., U.S.A. The brackets 63 are preferably formed from a strong substance, such as polycarbonate, aluminum, stainless steel, or any other material capable of supporting the scaffold. In addition, certain testing conditions may require holding the temperature of the environment at a particular temperature, such that the thermal conductivity of the brackets may be selected to increase or decrease the flow of heat to or from the scaffold. Although the brackets 63 are depicted as opaque in FIGS. 1–3, one skilled in the art would readily understand that the brackets may be transparent.

A synthetic sheet 81 mounts on the scaffold 33 for testing the material 23. The synthetic sheet 81 is preferably cut to size before mounting on the scaffold 33. The synthetic sheet 81 should be sized larger than the expected contact area between the test material 23 and the synthetic sheet, so that the test material contacts the synthetic sheet only, rather than the scaffold 33 or base 25 of the testing apparatus 21. The synthetic sheet 81 may be attached to the scaffold 33 using any conventional attachment means that do not interfere with the inherent properties of the synthetic sheet or operation of the apparatus 21. One such attachment means is adhesive.

In one embodiment, the synthetic sheet 81 comprises protein molecules and lipid molecules. An example of such a synthetic sheet 81 is Vitro-Skin®, designated N-19-5X, available from Innovative Measurement Solutions Inc. (IMS) of Milford, Conn., U.S.A. Vitro-Skin® effectively mimics the surface properties of human skin. It contains both optimized protein and lipid components and exhibits a topography, pH value, critical surface tension, ionic strength, chemical inertness and elasticity similar to human skin. Synthetic sheets 81 other than Vitro-Skin® may be used. In one alternative embodiment, sheets other than Vitro-Skin® but having similar topography, pH value, critical surface tension, ionic strength, chemical inertness, elasticity and dynamic and static frictional characteristics may be used.

As discussed previously, synthetic sheet 81 by itself, does not provide an adequate simulation of human skin for correlation of in vivo and in vitro testing. To further enhance the ability of the synthetic sheet 81 to simulate human skin, a porous layer 85 is applied to an exposed surface 91 of the synthetic sheet. The porous layer 85 may be a sheet-like substance, a liquid, or a cream. As with the synthetic sheet 81, the porous layer 85 must be sized and shaped to cover an adequate portion of the synthetic sheet, so that the test material 23 contacts only the porous layer, rather than the scaffold 33. The synthetic sheet 81 and porous layer 85 cooperate to form the simulated human tissue 41 used to evaluate the coefficient of friction between the test material 23 and the simulated human tissue. The simulated human tissue 41 accurately approximates the coefficient of friction that would be developed between the test material 23 and natural human skin. It is also contemplated within the scope of the present invention that the porous layer 85 may be integrally formed with the synthetic sheet 81. For example, the porous layer 85 may be applied to the synthetic sheet 81 during manufacture of the synthetic sheet, rather than when using the synthetic sheet for testing.

In one embodiment, the porous layer 85 applied to the synthetic sheet 81 is a sheet-like substance 85a. Such a porous layer 85a may comprise an elastomer, such as a silicone (e.g., identification number 9402, available from Dow Corning of Midland, Mich., U.S.A.). Other elastomers are also contemplated as being within the scope of the present invention. Alternately, the porous layer 85 may comprise a barrier cream 85b applied to the synthetic sheet 81. Barrier creams 85b are protective creams for use with human skin that help prevent and relieve chapping and irritation from frequent hand washing and latex glove use. When applied to the synthetic sheet 81, the barrier cream 85b allows water to permeate and retains such water at the exposed surface 91 of the synthetic sheet 81. This interaction mimics the natural barrier provided by human skin. An example of one such barrier cream is SoftGuard® barrier hand cream, available from Stahmer, Weston and Company, Inc. of Portsmouth, N.H., U.S.A.

Once the scaffold 33 and simulated human tissue 41 are configured as described above, the test material 23 may be placed into engagement with the simulated human tissue. Generally speaking, the load cell 29 is operatively connectable between the synthetic sheet 81 and the test material 23 for measuring the coefficient of friction between the synthetic sheet and the test material. A cable 95 extends generally horizontally from the load cell 29 and attaches to the test material 23 via an elongate upper support gusset 99.

The gusset spreads the load over the test material 23 to help prevent tearing. The test material 23 extends horizontally from the upper gusset 99 and passes over the simulated human tissue 41, engaging the porous layer 85 of the simulated human tissue for testing. A lower support gusset 103 attaches to the opposite end of the test material 23 and a mass 107 hangs from the lower gusset. This mass 107 holds the test material 23 and cable 95 in tension and pulls the test material against the simulated human tissue 41 during testing. The tension induced by the hanging mass 107 also presses the test material 23 into the simulated human tissue 41, so that the test material applies a known normal and constant force upon the simulated human tissue 41.

To evaluate the coefficient of friction between the simulated human tissue 41 and the test material 23, the test apparatus 21 moves the test material relative to the scaffold 33 to measure the frictional force between the test material and the simulated human tissue with the load cell 29. Because the normal force applied by the mass 107 is known and constant, the frictional force measured by the load cell 29 is proportional to the coefficient of friction. Typically, the scaffold 33 and simulated human tissue 41 remain stationary, while the load cell 29 pulls the test material 23 across the simulated human tissue. However, any relative motion between the test material 23 and the simulated human tissue 41 may be used to create friction.

Although various testing protocols are contemplated as being within the scope of the present invention, the following protocol was followed when evaluating the claimed invention. First, the simulated human tissue 41 and apparatus 21 are prepared as described above. For ten seconds, the load cell 29 collects load data from the test material 23 to determine the static loading on the test material. This loading corresponds to the force of gravity on the mass 107, minus any static frictional forces between the tested simulated human tissue 41 and the test material 23. In the absence of friction, the force on the load cell 29 would theoretically be equal to the force of gravity acting upon the mass 107. With friction, the load on the load cell 29 is less than the force of gravity acting upon the mass 107. After ten seconds, the load cell 29 moves the cable 95, the upper gusset 99 and the test material 23 horizontally so that the test material passes over the simulated human tissue 41. In one embodiment, the test material 23 moves at a rate of about 200 millimeters per minute. As the test material 23 moves over the simulated human tissue 41, the load cell 29 records the load exerted on the load cell over time. This baseline wipe records the friction between the simulated human tissue 41 and the test material when the simulated human tissue is dry.

After the baseline wipe test, a first wipe test is run with a new piece of test material 23 connected to the load cell 29 and mass 107 as before. Here, about a 0.5 cubic centimeter portion of Feclone-16, a fecal simulant, available from SiliClone Studio, of Valley Forge, Pa., U.S.A., is applied to the simulated human tissue 41 in a thin layer. The fresh test material 23 is then laid across the simulated human tissue 41 for engagement with the Feclone-16. The friction test is run exactly as noted above and the loads recorded over time. A second wipe test is run as above with another portion of fresh test material 23, but without reapplying the Feclone-16. Each portion of test material 23 is weighed before and after each wipe, so that the amount of Feclone-16 removed by each wipe may be calculated. The frictional properties of different kinds of test materials 23 may be tested using the method described above. For example, bath tissue, such as Cottonelle® bath tissue, available from the Kimberly-Clark Corporation of Neenah, Wis., U.S.A., or moistened baby wipes, such as Huggies Original® baby wipes, also available from the Kimberly-Clark Corporation, may be tested using this method.

Figure 4:
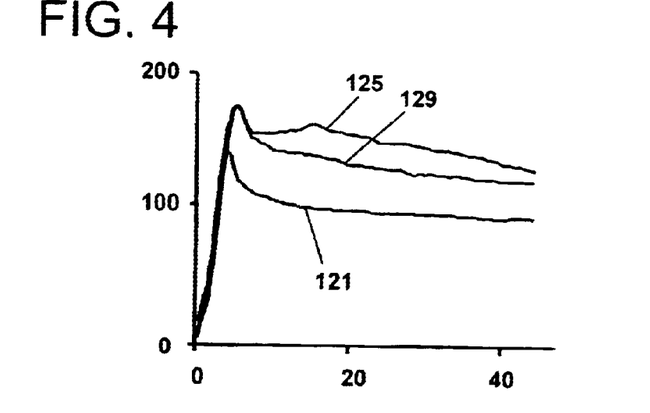
FIG. 4 is a graph depicting the frictional load between a portion of dry bath tissue and a portion of human skin.
Figure 5:
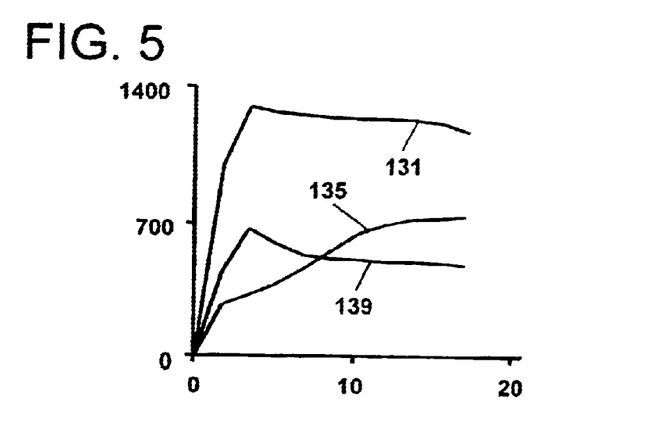
FIG. 5 is a graph depicting the frictional load between a portion of dry bath tissue and a portion of synthetic sheet.
Figure 6:
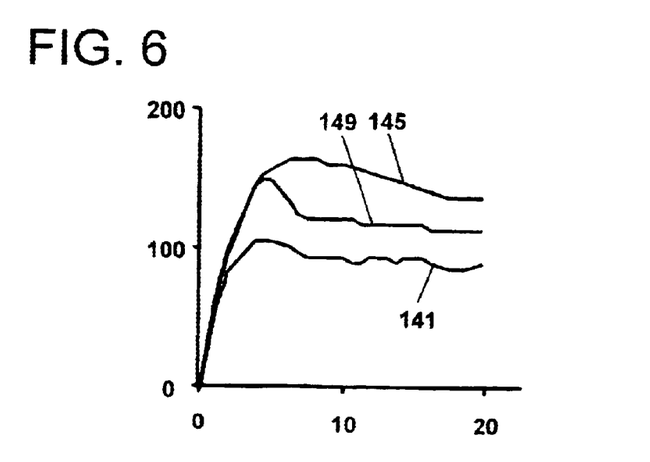
FIG. 6 is a graph depicting the frictional load between a portion of dry bath tissue and a portion of simulated human tissue.

FIGS. 4–9 demonstrate the ability of the simulated human tissue 41 to accurately predict the coefficient of friction of the test material 23 on human skin. FIGS. 4–6 depict three tests where the test material 23 used was Cottonelle® bath tissue. For each type of skin, or skin substitute, tested (human skin, synthetic sheet 81 or simulated human tissue 41), a baseline test was run where the test material 23 was attached to the load cell 29, placed over the skin, or skin substitute, and the mass 107 was attached to the free end of the test material. When testing with human skin in vivo, a living person's arm was placed adjacent the apparatus 21 for testing.

By comparing the loads recorded during the baseline test with the loads recorded during the two wiping tests, the dynamics of the wiping may be understood. For example, FIGS. 4–6 depict load versus time curves for the tests noted above. For each of FIGS. 4–9, the vertical axis of the chart indicates load in grams force, while the horizontal axis indicates time in seconds. The maximum values shown on the load scales and time scales vary from figure to figure. FIG. 4 depicts three tests where the test material 23 is bath tissue and the tested skin is human skin. The results of the baseline wipe test 121, a first wipe test 125 and a second wipe test 129 are each depicted on FIG. 4. The load on the test material 23 during the baseline wipe test 121 is the lowest. The load during the first wipe test 125 is greater than the load during the baseline wipe test 121, indicating that the addition of Feclone-16 has increased the friction between the baseline wipe and the first wipe. The second wipe test 129, however, yields a load less that the first wipe test 125, yet greater than the baseline wipe test 121, indicating that the friction between the human skin and the test material 23 has decreased toward the baseline reading.

Comparing FIG. 5 with FIG. 4 demonstrates the lack of correlation between synthetic sheet 81, used alone, and human skin. With the synthetic sheet 81, the first wipe test 135 and second wipe test 139 both indicate lower friction levels than the baseline wipe test 131. These results are inconsistent with human skin, where the first and second wipe tests 125,129 indicate a higher level of friction than the baseline wipe test 121. As such, the synthetic sheet 81 provides results inconsistent with human skin.

Comparing FIG. 6 with FIG. 4 demonstrates a correlation between the human skin tests and the simulated human tissue 41 tests. With the simulated human tissue, the first wipe test 145 exhibits a higher level of friction than the second wipe test 149; and both first and second wipe tests exhibit higher levels of friction than the baseline wipe test 141. The baseline, first and second wipe tests 141,145,149 each indicate an appropriate level of friction with respect to one another. As such, the simulated human tissue 41 provides a frictional response to wiping that is similar to human skin, making the simulated human tissue perform like human skin.

Figure 7:
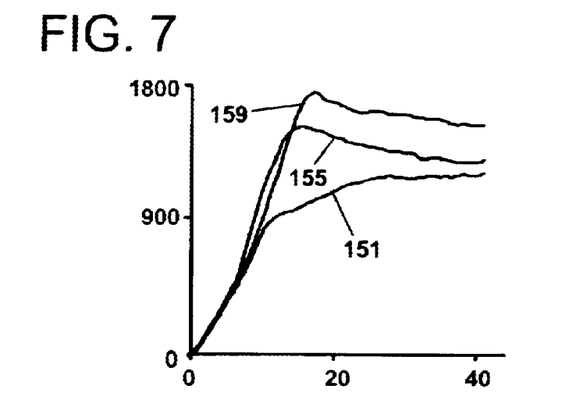
FIG. 7 is a graph depicting the frictional load between a portion of baby wipe and a portion of human skin.
Figure 8:
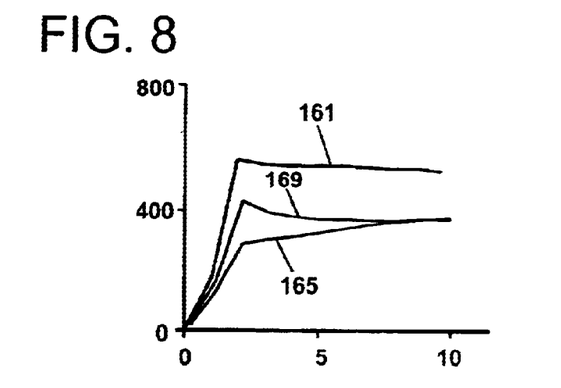
FIG. 8 is a graph depicting the frictional load between a portion of baby wipe and a portion of synthetic sheet.
Figure 9:
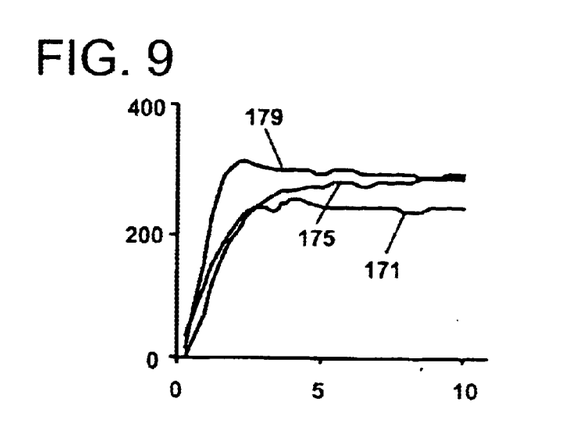
FIG. 9 is a graph depicting the frictional load between a portion of baby wipe and a portion of simulated human tissue.

FIGS. 7–9 depict load versus time curves for various tests involving baby wipes passed over human skin, synthetic sheet 81 or simulated human tissue 41. FIG. 7 depicts three tests where the test material 23, a baby wipe, interacts with human skin. The results of a baseline wipe test 151, a first wipe test 155 and a second wipe test 159 are each depicted in FIG. 7. The load on the test material during the baseline wipe test 151 is the lowest. The load during the first wipe test 155 is greater than the load during the baseline wipe test 151, indicating that the addition of Feclone-16 has increased the friction between the baseline wipe test and the first wipe test. The second wipe test 159 yields a load greater that the first wipe test 155 and the baseline wipe test 151, indicating that the friction between the human skin and the test material 23 has increased over the baseline and first wipe readings.

Comparing FIG. 8 with FIG. 7 demonstrates the lack of correlation between synthetic sheet 81, used alone, and human skin. With the synthetic sheet 81, the first wipe test 165 and second wipe test 169 both indicate lower friction levels than the baseline wipe test 161. These results are inconsistent with human skin, where the first and second wipe tests 155,159 indicate a higher level of friction than the baseline wipe test 151. As such, synthetic sheet 81 provides results inconsistent with human skin.

Comparing FIG. 9 with FIG. 7 demonstrates a correlation between the human skin tests and the simulated human tissue 41 tests. With the simulated human tissue, the first wipe test 175 exhibits a higher level of friction than the baseline wipe test 171, consistent with the human skin test of FIG. 7. The second wipe test 179 exhibits a higher level of friction than the baseline wipe test 171 and the first wipe test 175, also consistent with the human skin test. Because the baseline 171, first 175 and second 179 wipe tests each indicate an appropriate level of friction with respect to one another, the simulated human tissue 41 provides a frictional response to wiping that is similar to human skin, making the simulated human tissue perform like human skin.

In view of the above, it will be seen that the several objects of the invention are achieved and other advantageous results attained.

When introducing elements of the present invention or the preferred embodiment(s) thereof, the articles "a," "an," "the," and "said" are intended to mean that there are one or more of the elements. The terms "comprising," "including," and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. An in vitro testing method for predicting a coefficient of friction exhibited by a material passed over human skin, in vivo, said method comprising:

operatively connecting a material between a scaffold and a load cell;

mounting a synthetic sheet on the scaffold;

applying a porous layer to an exposed surface of said synthetic sheet to form a simulated human tissue;

engaging the material with said simulated human tissue; and moving the material relative to the scaffold thereby to measure said coefficient of friction between said material and said simulated human tissue with said load cell.

2. A method as set forth in claim 1 further comprising applying a force to said simulated human tissue in a direction normal to said simulated human tissue.

3. A method as set forth in claim 1 wherein said applying step comprises applying a sheet-like substance to said synthetic sheet.

4. A method as set forth in claim 1 wherein said applying step comprises applying a barrier cream to said synthetic sheet.

5. A testing apparatus for evaluating a coefficient of friction developed between a material and a simulated human tissue to approximate the coefficient of friction that would be developed between said material and natural human skin, said testing apparatus comprising:

a scaffold sized and shaped to simulate a portion of human anatomy;

a synthetic sheet mounted on said scaffold; and a load cell operatively connectable between said synthetic sheet and the material for which the coefficient of friction is being evaluated for measuring the coefficient of friction between said synthetic sheet and the material.

6. A testing apparatus as set forth in claim 5 further comprising a porous layer applied to an exposed surface of said synthetic sheet.

7. A testing apparatus as set forth in claim 6 wherein said porous layer comprises an elastomer.

8. A testing apparatus as set forth in claim 7 wherein said elastomer comprises silicone.

9. A testing apparatus as set forth in claim 6 wherein said porous layer comprises a barrier cream.

10. A testing apparatus as set forth in claim 5 wherein said scaffold is sized and shaped to simulate a human arm.

11. A testing apparatus as set forth in claim 10 wherein said scaffold is generally cylindrical in shape.

12. A testing apparatus as set forth in claim 11 wherein said scaffold comprises a plastic tube.

13. A testing apparatus as set forth in claim 11 wherein said generally cylindrical scaffold has an oval cross-section.

14. A testing apparatus as set forth in claim 13 wherein said scaffold has a height of about 7.6 centimeters and a width of about 10 centimeters.

15. A testing apparatus as set forth in claim 14 wherein said scaffold has a length of about 22.2 centimeters.

* * * * *

UNITED STATES PATENT AND TRADEMARK OFFICE
CERTIFICATE OF CORRECTION

| | |
|---|---|
| PATENT NO. | : 6,645,161 B2 |
| APPLICATION NO. | : 10/021286 |
| DATED | : November 11, 2003 |
| INVENTOR(S) | : Koenig et al. |

It is certified that error appears in the above-identified patent and that said Letters Patent is hereby corrected as shown below:

On the cover page,

[*] Notice: Subject to any disclaimer, the term of this patent is extended or adjusted under 35 USC 154(b) by (43) days Delete the phrase "by 43" and insert -- by 58 days--

Signed and Sealed this

Seventeenth Day of April, 2007

JON W. DUDAS
*Director of the United States Patent and Trademark Office*